TYPE 1 AND TYPE P FIMBRIAE-ADHESINS ISOLATED FROM NOVEL E. COLI STRAINS, PROCESS FOR THEIR PREPARATION AND USES THEREOF

(57) ABSTRACT

Fimbriae adhesins have a molecular weight of $2 \times 10^5$ and $2 \times 10^7$ Da, and are comprised of 90–95% protein and 1–3% sugar. Type 1 fimbriae include five different protein fractions of 14–20 kDa, most of which are associated with carbohydrates. Type P fimbriae also include five different protein fractions of 14–20 kDa, and one of the majority proteins is associated with carbohydrates. The process of the invention comprises: culturing *E. coli* strains CECT 4484 and CECT 4485; collecting the sediment by centrifugation and resuspending it in physiological saline followed by homogenization; centrifuging the homogenate and collecting the supernatant; precipitating the supernatant with saline, reconstituting the precipitate and dialyzing the solution; treating the dialyzate with sodium deoxycholate and, subjecting the product to two successive chromatographies with Sephacryl S-200 and Sepharose 4B. The product is used for treatment and prevention of infections of the urinary tract caused by fimbriated *E. coli*.

12 Claims, 4 Drawing Sheets

TYPE 1 AND TYPE P FIMBRIAE-ADHESINS ISOLATED FROM NOVEL E. COLI STRAINS, PROCESS FOR THEIR PREPARATION AND USES THEREOF

This application claims the priority of patent application Ser. No. 9400202 filed Feb. 4, 1994 in Spain. This is a continuation in part of Ser. No. 08/858,903, filed May 19, 1997, now abandoned, which was a continuation of Ser. No. 08/383,765, filed Feb. 3, 1997, now abandoned.

TECHNICAL FIELD OF THE INVENTION

The present invention fits into the technical field of products used for the treatment and prevention of urinary tract infections.

More specifically, the present invention relates to fimbriae, isolated in a highly purified state from *E. coli*, that have been shown to be effective for the aforementioned purposes in animals. Said fimbriae are thus potentially useful for the prevention and treatment of the cited infections in humans.

The *E. coli* strains used are *Escherichia coli* CECT 4484 and *Escherichia coli* CECT 4485 deposited by the applicant in the Spanish Culture Type Collection (Colección Española de Cultivos Tipo—CECT) of the University of Valencia Campus de Burjaset, L41600 BURJASET, Valencia, Spain on Jan. 19, 1994, in accordance with the "Budapest Treaty on International Recognition of the Deposit of Microorganisms for the purposes of the Process in Patent Material". Both are feasible strains for "Reseeding in suitable culture media".

PRIOR ART OF THE INVENTION

*Escherichia coli* is the most frequent etiological agent in infections of the urinary tract. Symptoms of such infection include acute and chronic cystitis, as well as pyelonephritis and asymptomatic bacteriuria ((1) "Problemática de las infecciones urinarias en España" (Problem of urinary infections in Spain) Liade, 1989; (2) Woodrow G C, Levine M M *New generation vaccines*, 1990).

Infections of the urinary tract are caused by *Escherichia coli* strains which contain adhesin structures that are capable of binding to the uroepithelial cells ((3) Johnson J W, Virulence factors in *E. coli* UTI. Clin. Microbiol. Reviews 1991; 4; 80–128). Said structures are one of the main causes of pathogenicity of these organisms in the urinary tract (3). These structures are comprised of protein subunits with a tubular shape that contain a terminal and/or side region where they combine with the receptor ((3) and (4) Brinton C C. The structure, function, synthesis and genetic control of bacterial pili and molecular model for DNA and RNA transport in gram negative bacteria. Trans NY Acad. Sci. 1965; 27; 1003–1054). Said structures are named fimbriae and several families which are associated with factors of virulence, such as mannose resistant fimbriae (type P:P, F or NAP, type X or Dr related; 5, M, 6) and mannose sensitive fimbriae (type 1), have been identified (3). Type X, AFA-I and AFA-III mannose resistant adhesins are not associated with fibrial structures. Type 1 and Type P fimbriae have been tested for use as agents to prevent and/or protect against infection of the urinary tract by uropathogenic *E. coli* ((5) Hagberg L, Leffler H, Svanborg-Eden C. Non-antibiotic prevention of UTI: Infection 1985; 13 (Suppl. 2): 196–200; (6) O'Hanley P. Lark D, Falkow S, Schoolnik G. Molecular basis of *E. coli* colonization of the upper urinary tract in Balb/c mice.—J. Clin. Invest. 1985; 75: 347–360; (7) Hutlgren S J, Porter T N, Schaeffer A J, Duncan J L. Role of type I pili and effects of phase variation on lower UTI produced by E. colo. Infect. Immun. 1985; 50: 370–377; (8) Silverblatt F S, Weinstein R. Rene P. Protection against experimental pyelonephritis by antibodies to pili. Science J. Infect Dis 1982; suppl. 33: 79–82).

The object of the present study was to purify fimbriae-adhesins of uropathogenic *E. coli* from urine samples of women with recurrent cystitis and to use the fimbriae as a product for preventive treatment of infections of the urinary tract.

Studies have already been conducted on the isolation of *E. coli* fimbriae and on the effectiveness of the use of fimbriae in vaccines for the prevention of urinary tract infections. Thus, aside from the publication of Pecha et al. ((9) Pecha B, Low D. O'Hanley P. Gal-Gal pili vaccines prevent pyelonephritis by piliated *E. coli* in murine model. J. Clin. Invest. 1989; 83:2102–2108), the following documents may be cited:

Patent DE3832785 regarding the isolation of p-adhesin from *E. coli* cells and use of the same for immunization, production of antibodies and diagnosis.

Patent EP-342173 regarding a new fibronectin bonding protein expressed as fimbria on *E. coli* and hybrid DNA encoding sequences, to prevent *E. coli* infections by means of vaccination or topical application.

Patent EP-314224 regarding a vaccine for the protection of fowl against septicemia by *E. coli* that contains immunogenic sections or type F11 fimbriae or antibodies against them.

Patent EP-249739 regarding a vaccine for immunization against infections of the urinary tract that comprise fimbriae with fimbriae of the same fimbric family as the infecting organisms.

Patent EP-179887 regarding an antigen that comprises a polypeptide adhesin determinant, useful in immunization against bacterial infections and in the production of antibodies for diagnosis of infections.

Patent EP-161095 regarding vaccines against urinary tract infections containing fragments of proteins of gal-gal fimbriae of *E. coli*.

U.S. Pat. No. 0,546,584 regarding the preparation of vaccines from *Escherichia coli* with pharmacological uses to prevent or cure gastroenteritis.

In contrast to the disclosures of the above-cited documents, the present invention relates to the preparation and purification of Type 1 and Type P fimbriae-adhesins from *E. coli* strains isolated from the urine of women with recurrent cystitis. By means of the present invention it is possible to obtain intact fimbriae-adhesins, free from other proteins or structures that could affect the metabolism or localization of the product after administration to a subject, such as flagella, hemolysin and LPS. This ensures the elimination of toxic substances that may be associated with the final product.

The absence of cross reactivity between type 1 fimbriae-adhesins and type P fimbriae-adhesins allows the separate production of immunogens to each of the types of fimbriae. The two types of fimbria-adhesins may also be used to produce immunogens at equal concentrations.

Verification of the adherence capacity of the *E. coli* strains associated with the fimbriae allows one to work with a material that induces an immune-response against the adhesin fraction that causes the fixation of *E. coli* to uroepithelial cells.

SUMMARY OF THE INVENTION

In one aspect, the present invention relates to composition comprising a member selected from the group consisting of an intact Type P fimbriae isolated from *E. coli* CECT 4484, an intact Type I fimbriae isolated from *E. coli* CECT 4485, and mixtures thereof, where the fimbriae have a molecular weight of between $2 \times 10^5$ and $2 \times 10^7$ daltons and are comprised of 90–95% by weight of protein and 1–3% by weight of sugar, each of the fimbriae comprising protein fractions of 5 different molecular weights, wherein the five protein fractions of type 1 fimbriae have molecular weights of between 14 and 20 kDa, with a fraction of the type 1 fimbriae with a molecular weight of 17 to 18 kDa comprising about 55% of the protein of the type 1 fimbriae, wherein the five protein fractions of type P fimbriae have molecular weights between 14 and 20 kDa and comprise a fraction having a molecular weight of 19 to 20 kDa wherein the fraction comprises about 35% of the protein of the type P fimbriae, wherein the 17 to 18 kDa fraction of the type 1 fimbriae and the 19 to 20 kDa fraction of the type P fimbriae are linked to carbohydrates, wherein the carbohydrates contain mannose-mannose units $\alpha(1-3)$, $\alpha(1-6)$, or $\alpha(1-2)$, $\alpha$ sialic acid, $\alpha(2-6)$, or $\alpha(2-3)$ galactose, galactose $\beta(1-3)$ n-acetyl galactosamine, and galactose $\beta(1-4)$ n-acetyl glucosamine.

In another aspect, the invention is directed to methods for the purification of fimbriae adhesins from strains CECT 4484 and CECT 4485 of *E. coli*, the process comprising:

a) seeding bacteria of strains CECT 4484 and CECT 4485 of *E. coli* in a liquid culture medium at about 37° C. until cultures are obtained at the beginning of the stationary phase ($10^8$–$10^9$ ucf/ml);

b) centrifuging the cultures and washing the obtained sediment;

c) resuspending the sediments washed in a physiological saline solution with a neutral pH and cold homogenizing same in a shear homogenizer for 2 to 10 minutes, at a speed of 10,000 to 25,000 rpm;

d) centrifuging the homogenates thus obtained at some 25,000–45,000×g for 20–45 minutes, discarding the sediment containing the bacteria and retrieving the supernatant liquid;

e) subjecting the supernatant liquid containing the fimbriae to several cold saline precipitations for a time period between 2 and 15 hours, retrieving the precipitate by centrifugation;

f) reconstituting the precipitate thus obtained in an aqueous physiological solution of a neutral pH and dialyzing the obtained solution;

g) treating the dialyzed solution containing the fimbriae with sodium deoxycholate 5% at about 80° C.;

h) subjecting the product resulting from the previous step to chromatography in a gel filtration column containing Sephacryl S-200 and subjecting the chromatographed product located in the exclusion volume to another chromatography in a column containing Sepharose 4B, and collecting the inclusion volume to obtain the fimbriae.

In yet another aspect, the invention is directed to methods for the prevention and treatment of urinary tract infections caused by fimbriated *E. coli*.

DETAILED DESCRIPTION OF THE INVENTION

Figure 1:
FIG. 1 is a microphotograph taken by electron microscopy techniques, of the purified fimbriae from the *E. coli* strain CECT 4484.

The present invention relates to Type 1 and Type P fimbriae-adhesins isolated from *E. coli* strains, a process for their preparation and the uses thereof.

The process of the present invention is based on the classic process described by Brinton (4). However in the present invention, novel strains of uropathogenic *E. coli*, isolated from urine of women with recurrent cystitis, were used as the starting material. It was verified that adhesins were associated with Type 1 and Type P fimbriae. *E. coli* strains CECT 4484 and CECT 4485, whose characteristics are indicated in the following table 1, were used:

TABLE 1

Uropathogenic *E. coli* strains CECT 4484 and CECT 4485 Main subunit Fimbria/PM

| Source | Serotype | kDA | Hemolysin | Adherence |
|---|---|---|---|---|
| strain CECT 4484 | Urine ♀ 04:K- | P/17.5 | + | >100 bact/epithelial cell |
| strain CECT 4485 | Urine ♀ 05:K13 | 1/18.5 | + | >100 bact/epithelial cell |

The bacteria are inncoulated in a liquid culture medium and grown at 37° C. until the beginning of the stationary phase ($10^8$–$10^9$ cfu/ml).

The cultures are centrifuged and the sediment is washed by means of centrifugation, for the purpose of eliminating the culture medium and the components that may exist in it.

The washed sediments containing the bacteria are resuspended in physiological saline solution with a neutral pH and cold homogenized, in a shear homogenizer from 2 to 10 minutes, at a speed of 20,000 to 25,000 rpm.

The homogenates are centrifuged at 25,000–45,000×g for 20–45 minutes and the sediment containing the bacteria is discarded.

The supernatant containing the fimbriae is recovered and several cold saline precipitations are performed (for example with $MgCl_2$ or $(NH_4)_2SO_4$). The precipitations can be carried out for periods of 2 hours to overnight.

The precipitated material is recovered by means of centrifugation. It is reconstituted in aqueous physiological solution of a neutral pH and afterwards it is dialyzed for the purpose of eliminating residual salts and molecules smaller than 10,000 Da.

The fimbriae are treated with sodium deoxycholate 5% at about 80° C. for the purpose of eliminating the lipopolysaccharides (LPS).

The material thus obtained (intact fimbriae) is subjected to chromatography in a gel filtration column containing Sephacryl S-200 (matrix for chromatography formed by a covalent linkage of allyl-dextran with N,N-methylenebisacrylamide, that gives rise to a rigid mesh in the form of spheres of 25–75 μm with pores that permit the inclusion of proteins of 1,000 to 80,000 Da) and the exclusion volume obtained therefrom is subjected to chromatography in a Sepharose 4B column (matrix for chromatography formed by spheres of agarose of 45–165 μm with very little residue of groups with filler and pores that permit the inclusion of proteins of $6×10^4$ to $20×10^6$ Da), for the purpose of obtaining intact fimbriae free of large substances, such as flagella or remains of membranes, etc., or of toxic substances with intermediate or low molecular weights, such as hemolysin, LPS, etc. that could affect the metabolism or localization of the product after administration to a subject. The elimination of toxic substances that might be present in the final product is thus ensured.

The material contained in the inclusion volume of the Sepharose 4B column constitutes the product of the present invention, and has a molecular weight between $2×10^5$ Da and $20×10^6$ Da.

Practically no cross reactivity occurs between the Type 1 and the Type P fimbriae-adhesins isolated according to the present invention. This allows the manufacture of immunogens that possess each of the types of fimbria separately, as well as immunogens that possess both types of fimbriae-adhesins in equal concentrations.

In addition, the verification of the adherence capacity of the E. coli strains allows one to work with a material that induces an immune response against the adhesin fraction which causes the fixation of E. coli to uroepithelial cells.

The characteristics of the fimbriae were studied by determining the total sugar content, by the sugar reduction method ((10) Park J T. Johnson M J. A subminodetermination of glucose. J. Biol. Chem. 1949; 181:149–151; and (11) Chaplin M F. Kennedy J F Carbohydrate analysis. A practical approach. IRL Press. Oxford. Washington, D.C. (1986)), as well as the total protein content, by the Sutherland method ((12) Sutherland E W Cosi C F. Haynes R, Olson N S. Purification of the hyperglycemic-glycogenolitis factor from insulin and from gastric mucosa. J. Biol. Chem. 1949; 180:825–837) or by UV spectrophotometry.

By the above methods the fimbriae obtained by the process of the present invention were shown to be comprised of 90–95% by weight of proteins and 1–3% by weight of sugar.

The degree of polymerization of the fimbria was determined by spectrophotometric measurement of the sample in the range of wave length that comprises the UV region (350–195 mm) (4.)

SDS-PAGE analysis performed according to the methods of Mc. Michael ((13) Mc. Michael J. Ou. JT. Structure of common pili from E. coli J. Bacteriol. 1979; 138:969–975) revealed the presence of fimbria fractions (that can be differentiated from the membrane proteins) due to their distinct electrophoretic mobility in the presence or absence of 2-β-mercaptoethanol. This allowed differentiation between the different types of fimbriae.

The detection and differentiation of carbohydrates by means of immunodetection with lecithins was performed according to J. Montreuil et al. ((14) Montreuil J. Bouquelet S, Debray H. et al. Glycoproteins. Chapter 5 in M F Chaplin and J F Kennedy. Carbohydrate analysis. 1986. IRL Press. Oxford, Washington, D.C.). Carbohydrates were associated with specific fractions of fimbriae, as determined by electrophoresis, as follows:

Type 1 fimbriae contained 5 different protein fraction with molecular weights between 14 and 20 kDa, with a majority fraction (about 55% of protein in Type 1 fimbriae) of 17–18 kDa that was linked to carbohydrates;

Type P fimbriae contained 5 protein fractions with molecular weights between 14 and 20 kDa, with a fraction of of 19–20 kDa that comprised about 35% of the protein in the Type P fimbriae, and a 15 kDa fraction that comprised about 30% of the protein in the Type P fimbriae, of which the 19–20 kDa fraction was linked to carbohydrates.

Gel filtration chromatography by means of the SMART SYSTEM revealed the capacity of the pilin subunits to reorganize to form high molecular weight fimbriae, and allowed the subsequent purification thereof.

Analysis of the carbohydrates associated with fimbriae-adhesins by means of immunodetection with lecithins showed that said carbohydrates have mannose-mannose units $α(1-3)$, $α(1-6)$ or $α(1-2)$, sialic acid $α(2-6)$ or $α(2-3)$ galactose, galactose $α(1-3)$ n-acetyl galactosamine, galactose $α(1-4)$ n-acetyl glucosamine.

Chromatographic analysis of fimbriae-adhesins, as well as of the protein subunits of which they are comprised showed that when the fimbriae were kept in suspension in aqueous solutions the subunits rapidly reorganized to form units of fimbriae and/or aggregates of high molecular weight. The fimbriae separated into subunits of 14–20 kDa in the presence of alkaline solutions, anionic detergents, 2-β-mercaptoethanol, or high temperatures (100° C.)

The purified Type 1 and Type P fimbriae have the same characteristics when they are associated with the bacterial body, hemagglutination and agglutination of S. cerevisiae (type 1) ((3) and (15) Domingue G J, Roberts J A, Lauciria R. Pathogenic significance of O. fimbriated E. coli in urinary tract infections. J. Urology 1985; 133:983–989) and PPA technique, "receptor-specific" particle agglutination ((16) Svenson S B, Kallenius G. Möllby R, Huttberg H. Winberg J. Rapid identification of P. fimbriated E. coli by a receptor-specific particle agglutination test. Infection 1982; 10:209–213).

The intact fimbriae-adhesins obtained by the process of the present invention from E. coli strains with Type 1 fimbriae (CECT 4485) and Type P fimbriae (CECT 4484), isolated from urine of women with recurrent cystitis, have important uses as immunogens and constitute the product used in this invention as the immunogen for obtaining polyclonal or monoclonal antibodies.

Both the polyclonal and monoclonal fimbriae-adhesin antibodies have practically no cross reactivity. Said antibodies can be used as diagnostic tools to identify the type of uropathogenic E. coli fimbriae-adhesins. In addition, the use of intact fimbriae-adhesins as protective agents against UTI has proven to be effective during active immunization with said components. The specific products that have been used therapeutically in the prevention of urinary tract infections produced by uropathogenic E. coli are: (1) intact fimbriae in aqueous suspension, (2) fimbriae with coadjuvants, whether adsorbed to aluminum hydroxide gel or bonded covalently to high molecular weight polysaccharides (such as for example pululan which is a linear glucose polymer (maltotriose) produced by Aureobosidium pullulans) and (3) in nanoparticles orally.

Experimental studies of the induction of a specific immune response against intact fimbriae demonstrated an effective humoral immune response by the production of specific antibodies. The early induction of the natural cellular immune response was demonstrated by means of histopathological studies. The presence of inflammatory infiltrates with the accumulation of white blood cells (macrophages and lymphocytes) indicates the beginning of specific immune cellular response subsequent to the urinary tract infection.

Immunization with Type 1 and Type P fimbriae prior to UTI in mice causes significant differences between experimentally infected groups, depending on whether or not they have been previously immunized. Therefore it can be concluded that this type of active immunization causes a specific protection from UTI caused by uropathogenic E. coli strains.

The specific polyclonal (anti-fimbriae) antibodies obtained in mice are capable of inhibiting the adhesion capacity of Type 1 and Type P fimbriae-adhesins.

The intact immunogens (fimbriae) or immunogens with adjuvants are administered in the form of aqueous suspensions (saline solution buffered with merthiolate 0.01%) that have proven effective in a broad range of doses 0.1 µg–100 µg/kg weight, administered in 1 to 4 doses, spaced in time with a minimum of 30 days (as long as more than one dose is administered). The adjuvants normally used are aluminum hydroxide gel, calcium phosphate gel and pululan.

The immunogens are normally administered subcutaneously and intraperitoneally.

Other modes of administration such as oral, in capsules or microparticles, as well as intraurethrally in suspension form, cannot be excluded.

Embodiments of the Invention

The present invention is additionally illustrated by means of the following Example, which does not aim to restrict the scope thereof.

EXAMPLE

Strains and Characteristics of the Same

E. coli strains, identified as possessing fimbriae by means of agglutination techniques in the presence or absence of mannose and adhesion capacity to human uroepithelial cells, were isolated from the urinary tract of women with recurrent cystitis. The present serotypes were characterized by means of specific immunoserums and the production of hemolysin in agar blood cultures was measured. The following strains were selected:

| Strain | Serotype | Fimbria Type | Adherence | Hemolysin |
|---|---|---|---|---|
| IA1P10 | 07:K1 | 1 and P | 89 bact/cell | – |
| IA1P2H | 06:K2 | 1 and P | >100 bact/cell | + |
| CECT 4485 | 05:K13 | 1 | >100 bact/cell | + |
| IA10H | 083:K- | 1 | >100 bact/cell | – |
| CECT 4484 | 04:K- | P | >100 bact/cell | + |
| IAX130 | 025:K13 | X | 57 bact/cell | + |

Method of Preparation and Characterization

Uropathogenic E. coli strains were inoculated in nutritive broth and were incubated overnight at 37° C. One ml of these cultures ($10^8$–$10^9$ cfu/ml) was inoculated in 50 ml of nutritive broth, and incubation at 37° C. was carried out overnight, without stirring. The cultures were centrifuged at 10,000–20,000×g for 20 minutes, three times, for the purpose of eliminating the culture medium, and the precipitate was resuspended in sterile saline solution (SS) (45 ml/500 ml culture). The bacteria in SS were cold homogenized (4° C.) in a mechanical shear homogenizer, with 4 pulses of 1 minute at 18,750 rpm with intervals of 3 minutes between pulses. (Virtishear-24 homogenizer with macro assembler and shears). The homogenized material (bacteria and fimbriae separated from the bacteria) was cold centrifuged at 10,000×g for 20 minutes. The supernatant containing the fimbriae was purified by saline precipitation carried out with cold $MgCl_2$ (20.3 g of $MgCl_2.3H_2O$/Liter of supernatant). The precipitate was recovered by centrifugation (20,000×g, 30 minutes at 4° C.) and resuspended in PBS 0.02 M pH=7.4. The saline precipitation was repeated 3 times. The material (fimbriae) was resuspended in PBS after the last precipitation and was dialyzed exhaustively against distilled water.

The fimbriae thus isolated were treated with sodium deoxycholate 5% at a temperature of 80° C. for 15 minutes and were dialyzed again against distilled water.

The samples were passed through a Sephacryl S-200 HR column (XK26/100 Pharmacia) and were monitored with ISCO VA-5 equipment with a fraction retriever, Retriever II. Tris-HCl 50 mM pH=8 elution buffer was used, at a flow rate of 40 ml/h. The fractions corresponding to the elution volume were gathered and then passed through a column of the same characteristics and in the same conditions but with Sepharose 4B gel.

The inclusion volume was recovered and was exhaustively dialyzed against distilled, water. The fimbrial protein components of the inclusion volume from the Sepharose 4B gel column chromatography step constituted the material used for all of the subsequent experiments described herein.

The quantification of sugar (11) (sugar reduction method for quantification of monosaccharides by the neocuproine reagent) and of proteins (4) (spectrophotometric measurement at $\lambda$=280 nm with bovine serum albumin standards) in samples of fimbriae separated by heat and SDS, allowed determination of the yield of the process for preparation of fimbriae. The yield was found to be 3–10 mg of fimbrial proteins per liter of culture and 0.03–0.5 mg of monosaccharide sugar per liter of culture medium.

The treatment of the fimbriae according to the Mc Michael et al. method (13) allowed the evaluation of the protein components of said fimbriae. Briefly, the method comprises acidification of the sample to pH=2, heating for 10 minutes at 100° C., alkalinization of the sample to pH=10 followed by centrifugation and retrieval of the supernatant that was neutralized to pH=7. Precipitations were done with ammonium sulfate and the precipitate was resuspended in buffer sample Tris-HCl 0.5 M pH=6.8, SDS 10%-with and without 2-β-mercaptoethanol. The samples were heated to 100° C. for 2 to 10 minutes.

Electrophoresis in a discontinuous SDS-PAGE system at 12.5% was carried out based on the Laemmli method ((17) Laemmli UK. Cleavage of structural proteins during the assembly of the head of bacteriophage $T_4$. Nature 1970; 277:680–685).

The results showed a main band corresponding to more than 95% of all the fimbrial proteins, of Type 1 fimbriae proteins (19 kDa) as well as of Type P fimbriae proteins (18 kDa) with patterns that differed slightly between the two types of fimbriae, when said samples were heated for 2 minutes.

When the samples were heated for longer periods of time (10 minutes), the electrophoretic pattern of both types of fimbriae differed notably. Hence, Type 1 fimbriae showed 5 different fractions with molecular weights between 21 and 13 kDa with two majority bands (33% and 31%) of 19 to 15 kDa.

Type P fimbriae showed five bands between 20 and 14 kDa with a main component (53%) of 18 kDa.

The detection and differentiation of glycoproteins associated with pilin bands (11) by means of immuno-detection of lecithins by the method designed by Boehringer Mannheim (Glycan Detection Kit and Glycan Differentiation Kit), in fractions fixed to nitrocellulose membranes, showed the presence of sugars associated with the pilin bands in both types of fimbriae. The lecithins used recognized terminal mannose residues α(1-3), α(1-6), or α(1-2), bonded to mannose, sialic acid bonded to α(2-3) galactose and galactose β(1-3) N-acetylgalactosamine. The recognition may be at the terminal level as well as the middle level given the previous treatment to which the samples were subjected.

The presence or absence of 2-β-mercaptoethanol (2 βBE) determined whether the mobility of the 19 kDa and 18 kDa fractions of the Type 1 and Type P fimbriae, respectively, was altered. This indicates that the subunits form part of the fimbriae (13). Electrophotometric analysis in the ultraviolet range showed the presence of a relative maximum at 290 nm in fimbriae isolated directly from the preparation process. The maximum disappeared after treatment of the same with separating agents that characterize the integrity or degree of polymerization of the fimbriae.

Analysis by means of high resolution microchromatography by the SMART System (Pharmacia Biotech) with filtration microcolumns in Superdex 75 Pc 3.2 gel (30) according to the methodology proposed by the manufacturer, showed the aggregating characteristic of the pilin subunits in aqueous media. Pilin subunits separated by acid-base shocks, 2-β-mercaptoethanol, SDS, urea and/or heat, rapidly grouped together once the separating agents were removed. This indicates, as other authors (13) point out, the hydrophobic nature of these proteins.

Figure 2:
FIG. 2 is a microphotograph taken by electron microscopy techniques, of the purified fimbriae from the *E. coli* strain CECT 4485.

The electron microscopic transmission studies showed the presence of fimbriae in the two E coli strains studied (CECT 4484 and CECT 4485). The microphotographs of the purified fimbriae showed a high degree of purity of the same (FIGS. 1 and 2).

Experimental Study

For the purpose of determining the degree of protection that could be obtained by means of active immunization of animals with fimbriae, an experimental study with Balb/c mice was designed.

Four batches of 20 Balb/c female mice were used, as described in the protocol.

The study was carried out: (I) by DOT-ELISA techniques, as described in Bjerrum et al. ((18) Gordon J. Billing P. Dot-Immunoblotting. General principles and procedures. In Bjerrun O J and Heegaard N H. Eds. Handbook of Immunoblotting of proteins.

Vol. I. CRC Press 1988.PP. 27–30) to measure the level of specific antibodies (titer) from serum and urine; (II) by means of isolation (6) and identification (API System) of bacteria from necroscopic pieces. The identification of the type of fimbriae isolated from the E. coli was done by means of SDS-PAGE analysis of the fimbriae obtained from each isolation; and (III) by means of histopathological studies ((19) Bancroft J B, Stevens A (Ed.) Theory and Practice of Histological Techniques. 1982; 2nd. Edition. Churchill and Livingstone. Edimburgh) of the necroscopic pieces (kidneys and bladder).

Protocol of the Experimental Study:

| BATCH NO. | INDIVIDUALS | BREED DEF. OF BATCH | CHARACTERISTICS | SAMPLES STUDIED |
|---|---|---|---|---|
| 1 | 10 Females | BALB/c Control of healthy ones | Healthy mice, not immunized. not infected | Serum, bladder and kidneys |
| 2 | 20 Females | BALB/c Infection with E. coli 1A 1 3 H | Healthy mice, not immunized, infected with E. coli CECT 4485 | Post-infection serum, pre- and post-infection urine bladder and kidneys |
| 3 | 20 Females | BALB/c Infection with E. coli 1A P O H | Healthy mice, not immunized, infected with E. coli CECT 4484 | Post-infection serum, pre- and Post-infection urine bladder and kidneys |
| 4 | 20 Females | BALB/c Immunization and infection | Healthy mice, immunized with Fimbria 1 and Fimbria P and then infected with both strains (1:) | Postimmunization and post-infection serum, Pre- and Post-infection urine bladder and kidneys |
| 7 | 10 Females | BALB/c Mice immunized and not infected | Healthy mice, immunized with Fimbria 1 and Fimbria P | Pre- and Post-immunization urine blood days 0, 15 and 30, bladder and kidneys |

| INFECTION MODEL | |
|---|---|
| *No. Batches | 4 |
| *Size and Identification Batches | |
| SAMPLE BATCH HEALTHY | Batch No. 1. Not infected/not immunized. 10 animals |
| CONTROL BATCH INFECTED | Batch No. 2. Infected with E. coli CECT 4485 20 animals |
| CONTROL BATCH INFECTED | Batch No. 3. Infected with E. coli CECT 4484 20 animals |
| *Catheters | Sterile stainless steel 0.5 mm diameter |
| *Anesthesia | 0.15–0.20 ml. i.m. administration "Zoletil 20" (Tiletha mine + Zolazepam) 4 mg/ml |
| *Inoculum | E. coli CECT 4485 and CECT 4485 Bacto nutrient broth - CULTIVATED 24 H. 37° CENTRIFUGATION 10000 rmp/20'/4° C. SEDIMENT SUPERNATANT sterile ssf suspension 25 ml RECONSTITUTION |

-continued

|  |  |
|---|---|
|  | CENTRIFUGATION |
|  | 10000 rpm/29'/4° C. |
|  | SEDIMENT SUPERNATANT |
|  | SUSPENSION SSF AND |
|  | ADJUST TO $10^9$ ufc/ml |
|  | INOCULUM |
|  | Viability by means of seeding 1 drop of |
|  | Mac Conkey agar |
| IMMUNIZATION MODEL | |
| Animals | BALB-C female mice |
|  | CAGES: 5 animals |
|  | Age: 8–10 weeks |
|  | Average Weight: 20 g. |
| Identification | Digitalized: Batch/Cage/No. Mouse |
|  | Example: CODE B2C3M5 |
|  | Batch No. 2 |
|  | Cage No. 3 |
|  | Mouse No. 5 |
| IMMUNIZATION MODEL | |
| *No. Batches | 2 |
| *Size and Identification | |
| Batches: | |
| CONTROL BATCH - BATCH NO. 7 | Mice immunized with |
|  | Fimbriae 1 and P |
|  | 10 animals |
| TEST BATCH - BATCH NO. 4 | Mice immunized with |
|  | Fimbriae 1 and P and |
|  | infected with serotypes |
|  | CECT 4485 and CECT 4484 |
|  | 20 animals |
| *Way of Administration | SC in complete Freund |
|  | adjuvant |
| *Administration dose | 25 mcg type 1 Fimbriae |
|  | 4 |
|  | weekly |
|  | 25 mcg type P Fimbriae doses |
| ANIMAL IMMUNIZATION-INFECTION MODE CONTROLS | |
| *Urinary | Discard mice with positive urine culture from |
| control | samples of spontaneous urination. Urine |
|  | culture medium: Mac Conkey and Nutrient agar |
| *Infection | Catheterism through the meatus |
|  | urinarius and medium intravesical injection of |
|  | 0.1 ml of a suspension of bacteria adjusted to |
|  | 10 ufc/ml |
| *Autopsy | Killing: 72 h post-infection |
|  | vesical |
|  | Bloodletting: Puncture of the inside angle of |
|  | the eye with Pasteur pipettes in anesthetized |
|  | animal and pouring into Eppendorf tubes for |
|  | retraction of the clot and obtainment of serum. |
|  | Samples: Medium incision from the pelvis |
|  | to the base of the neck, extended upon the |
|  | paws, after disinfecting the skin with ethanol. |
|  | Additional medium incision to open so as to |
|  | have access to the abdominal cavity. |
|  | Obtainment of sterile urine: |
|  | Puncture bladder with a needle with a 0.5 mm |
|  | diameter and suction in a 1 ml. syringe for |
|  | subsequent culture thereof and identification |
|  | of antibodies. Obtainment of bladders: After |
|  | removing urine, the bladder was sectioned and |
|  | the bladder was removed at its base, |
|  | transferring it to a vial with buffered formol |
|  | for the history pathological study. |
|  | Obtainment of kidneys: |
|  | Dissection and removal of both kidneys and |
|  | sagittal cut of the same at the renal pelvis |
|  | level in two equal parts. Microbiological |
|  | analysis by smear of the surface of the cut |
|  | section on plates with Mac Conkey agar and |
|  | incubation 37° C. 24 h. Histopathological |
|  | analysis. |

-continued

OVERALL RESULTS OF THE STUDY OF EXPERIMENTAL INFECTION
IN THE DIFFERENT BATCHES OF MICE

| STRAIN AND BATCH NO. | TOTAL INOCULATED ANIMALS | TOTAL IMMUNIZED ANIMALS | TOTAL INFECTED ANIMALS (%) |
|---|---|---|---|
| CECT 4485 (BATCH 2) | 20 | 0 | 16 (80) |
| CECT 4484 (BATCH 3) | 20 | 0 | 8 (40) |
| CECT 4485 (BATCH 4) | 20 | 20 (FIMBRIA 1) | 7 (35) |
| CECT 4484 (BATCH 4) | 20 | 20 (FIMBRIA P) | 0 (0) |

The histopathological studies showed that inoculation of female mice through the urethra produced pyelitis, urethritis or acute cystitis.

In all cases, the inflammatory phenomena were limited to the transitional epithelium of the calyxes and the connective tissue subjacent to the same. Segmentary inflammatory phenomena of the proximal portion of the urethra were observed to a lesser degree. There were no foci of infection in the parenchyma.

Study of the Immune Response of the Mouse to Immunization with Fimbrial Antigens The humoral immune response was studied by measuring the titer and characteristics of the specific antibodies by means of the DOT-ELISA technique, as described by Gordon et al. (18) ELISA based on Muñoz et al. ((20) Muñoz C., Nieto A., Gaya A., Martínez J. Vives J. New experimental criteria for optimization of solid-phase antigen concentration and stability in ELISA. J Immunol. Methods 1986; 94: 137–144) and SDS-PAGE Immunoblotting ((21) Towbin H., Staehilin I., Gordon J. Electrophoretic transfer of proteins from polyacrylamide gels to nitrocellulose sheet: procedure and some applications. Proc. Natl Acad. Sci. USA 1979; 76:4350–4354).

The study of cross reactivity between Type 1 and Type p fimbriae was done by ELISA inhibition, according to the method described by Martinez J. Nieto A., Vives J. Torres J M. Application of ELISA inhibition to Aspergillus antigen standardization for immunodiagnosis. J. Med Vet Micol 1985; 23:317–320.

The results revealed a clear increase in the titer of specific antibodies in individuals who had negative values before immunization, up to titers (DOT-ELISA) of more than 1,280. Absorbance difference values (ELISA) of 1.5 at serum dilations of 1/1,000 were observed after three immunizations at semi-monthly intervals.

Immunoblotting showed specific reaction of the antibodies to fractions of 17 kDa (type 1) and of 19 kDa (type P), corresponding to the fundamental components of the fimbriae.

The study of crooss reactivity by ELISA did not show any significant cross reactivity.

Figure 3:
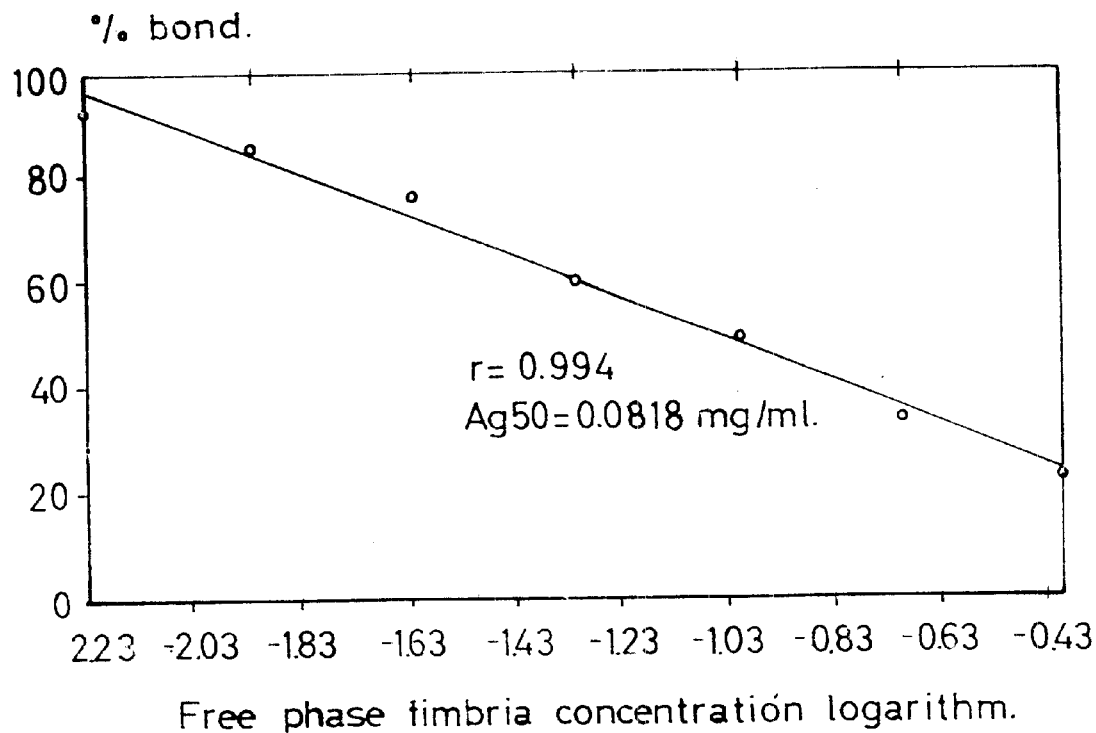
FIG. 3 is a graph of the results of the ELISA study of the inhibition of uropathogens with type 1 fimbriae in solid phase.
Figure 4:
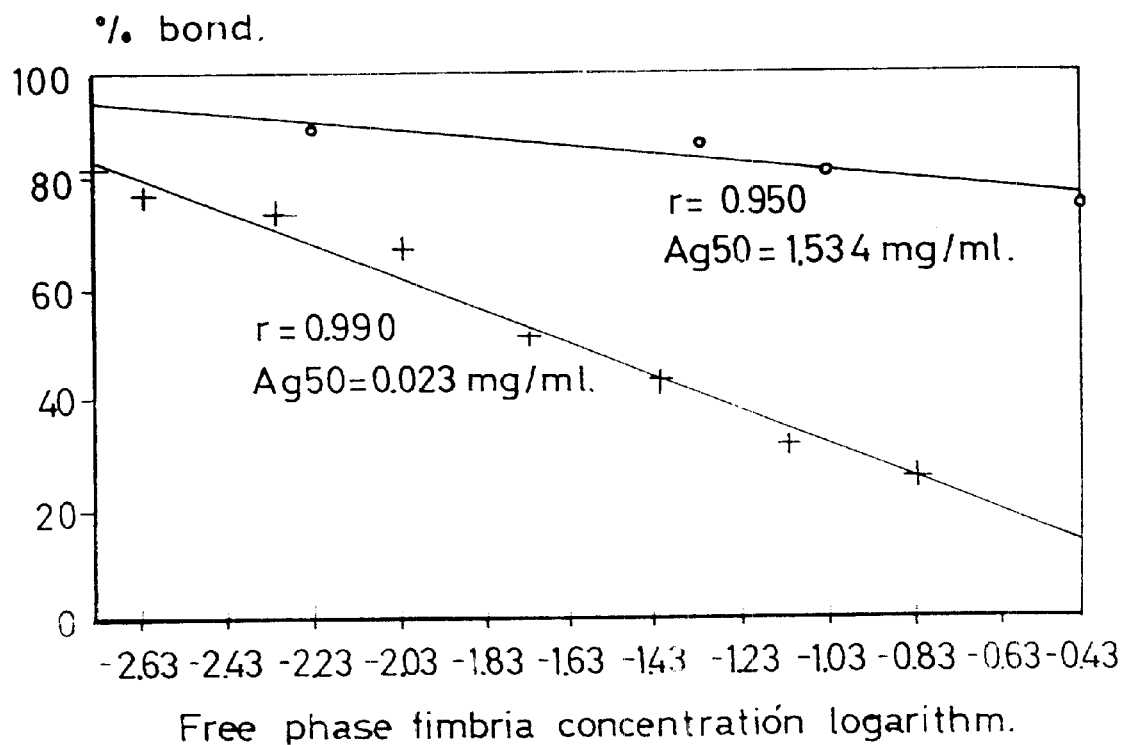
FIG. 4 is a graph of the results of the ELISA study of the inhibition of uropathogens with type P fimbriae in solid phase.

As can be seen in the graphs of FIGS. 3 and 4, no cross reactivity was observed between Type 1 fimbriae (solid phase) and Type P fimbriae (inhibitory phase). Very scarce cross reactivity (less than 2%) was detected between Type P fimbriae (solid phase) and Type 1 fimbriae (inhibitory phase). In both systems differences of $Ag_{50}$ were higher than $5 \times 10^3$.

The statistical analysis shown in the previous table (titled "Overall Results of the Study of Experimental Infection in the Different Batches of Mice") showed the existence of significant differences between the control uninfected batch, the infected batches and the batches immunized prior to infection.

Toxicity Test

Abnormal toxicity tests were carried out on guinea pigs (intraperitoneal administration), local tolerance subcutaneously on mice and abnormal toxicity in mice (intraperitoneal administration), according to standard protocols carried out by "Centro de Investigación y Desarrollo Aplicado, S. A. L." (Research and Applied Development Center, Ltd.) (homologated).

The results did not show any element that came into conflict with the rules of European Pharmacopeia, so as to include it as an unacceptable product.

What is claimed is:

1. A composition comprising a member selected from the group consisting of an isolated, Type P fimbriae isolated from *E. coli* CECT 4484, an isolated, Type I fimbriae isolated from *E. coli* CECT 4485, and mixtures thereof, said fimbriae having a molecular weight of between $2 \times 10^5$ and $2 \times 10^7$ daltons and being comprised of 90–95% by weight of protein and 1–3% by weight of sugar, each Type of said fimbriae comprising protein fractions of 5 different molecular weights, wherein the five protein fractions of Type 1 fimbriae have molecular weights of between 14 and 20 kDa, with a fraction of said Type 1 fimbriae with a molecular weight of 17 to 18 kDa comprising about 55% of the protein of said Type 1 fimbriae, wherein the five protein fractions of Type P fimbriae have molecular weights between 14 and 20 kDa and comprise a fraction having a molecular weight of 19 to 20 kDa wherein the fraction comprises about 35% of the protein of said Type P fimbriae, wherein said 17 to 18 kDa fraction of said Type 1 fimbriae and said 19 to 20 kDa fraction of said Type P fimbriae are linked to carbohydrates, wherein said carbohydrates contain mannose-mannose units $\alpha(1-3)$, $\alpha(1-6)$, or $\alpha(1-2)$, $\alpha$ sialic acid, $\alpha(2-6)$, or $\alpha(2-3)$ galactose, galactose $\beta(1-3)$ n-acetyl galactosamine, and galactose $\beta(1-4)$ n-acetyl glucosamine.

2. A composition according to claim 1, wherein said five protein fractions of said Type P fimbriae comprise a component having a molecular weight of 15 kDa, said 15 kDa component being unlinked to carbohydrates.

3. A composition according to claim 2, said 15 kDa component comprising 30% of the protein Type P fimbriae.

4. A composition according to claim 1, further comprising an adjuvant.

5. A composition consisting essentially of a member selected from the group consisting of an isolated, Type P fimbriae isolated from *E. coli* CECT 4484, an isolated, Type I fimbriae isolated from *E. coli* CECT 4485, and mixtures thereof, said fimbriae having a molecular weight of between $2 \times 10^5$ and $2 \times 10^7$ daltons and being comprised of 90–95% by weight of protein and 1–3% by weight of sugar, each Type of said fimbriae comprising protein fractions of 5 different molecular weights, wherein the five protein fractions of Type I fimbriae have molecular weights of between 14 and 20 kDa, with a fraction of said Type I fimbriae with a molecular weight of 17 to 18 kDa comprising about 55% of the protein of said Type I fimbriae, wherein the five protein fractions of Type P fimbriae have molecular weights between 14 and 20 kDa and comprise a fraction having a molecular weight of 19 to 20 kDa wherein the fraction comprises about 35% of the protein of said Type P fimbriae, wherein said 17 to 18 kDa fraction of said Type I fimbriae and said 19 to 20 kDa fraction of said Type P fimbriae are linked to carbohydrates, wherein said carbohydrates contain mannose-mannose units $\alpha(1\text{-}3)$, $\alpha(1\text{-}6)$, or $\alpha(1\text{-}2)$, $\alpha$ sialic acid, $\alpha(2\text{-}6)$, or $\alpha(2\text{-}3)$ galactose, galactose $\beta(1\text{-}3)$-N-acetyl galactosamine, and galactose $\beta(1\text{-}4)$ N-acetyl glucosamine.

6. The composition according to claim 5, wherein said five protein fractions of said Type P fimbriae comprise a component having a molecular weight of 15 kDa said 15 kDa component being unlinked to carbohydrates.

7. The composition according to claim 6, said 15 kDa component comprising 30% of the protein in the Type P fimbriae.

8. The composition according to claim 5 further comprising an adjuvant.

9. A process for the preparation of the fimbriae-adhesins, the process comprising:

(a) seeding *E. coli* bacterial strains CECT 4484 or CECT 4485, or both, in a liquid culture medium at about 37° C. until cultures are obtained at the beginning of the stationary phase ($10^8$–$10^9$ cfu/ml);

(b) centrifuging the cultures and washing the obtained sediment;

(c) resuspending the sediments washed in a physiological saline solution with a neutral pH and cold homogenizing same in a shear homogenizer for 2 to 10 minutes, at a speed of 10,000 to 25,000 rpm;

(d) centrifuging the homogenates thus obtained at a speed of 25,000 to 45,000×g for 20–45 minutes, discarding the sediment containing the bacteria and retrieving the supernatant liquid;

(e) subjecting the supernatant liquid containing the fimbriae to several cold saline precipitations for a time period between 2 and 15 hours, retrieving the precipitate by centrifugation;

(f) reconstituting the precipitate thus obtained in an aqueous physiological solution of a neutral pH and dialyzing the obtained solution against distilled water;

(g) treating the dialyzed, solution containing the fimbriae with sodium deoxycholate 5% at about 80° C.;

(h) subjecting the product resulting from the previous step to chromatography in a gel filtration column containing Sephacryl S-200 and subjecting the chromatographed product located in the exclusion volume to another chromatography in a column containing Sepharose 4B, and collecting the inclusion volume to obtain the fimbriae.

10. A process for the preparation of the fimbriae-adhesins, the process comprising:

(a) seeding *E. coli* bacterial strains CECT 4484 or CECT 4485, or both, in a liquid culture medium at about 37° C. until cultures are obtained at the beginning of the stationary phase ($10^8$–$10^9$ cfu/ml);

(b) centrifuging the cultures and washing the obtained sediment;

(c) resuspending the sediments washed in a physiological saline solution with a neutral pH and cold homogenizing same in a shear homogenizer for 2 to 10 minutes, at a speed of 10,000 to 25,000 rpm;

(d) centrifuging the homogenates thus obtained at a speed of 10,000×g for 20 minutes, discarding the sediment containing the bacteria and retrieving the supernatant liquid;

(e) subjecting the supernatant liquid containing the fimbriae to several cold saline precipitations for a time period between 2 and 15 hours, retrieving the precipitate by centrifugation;

(f) reconstituting the precipitate thus obtained in an aqueous physiological solution of a neutral pH and dialyzing the obtained solution against distilled water;

(g) treating the dialyzed solution containing the fimbriae with sodium deoxycholate 5% at about 80° C.;

(h) subjecting the product resulting from the previous step to chromatography in a gel filtration column containing Sephacryl S-200 and subjecting the chromatographed product located in the exclusion volume to another chromatography in a column containing Sepharose 4B, and collecting the inclusion volume to obtain the fimbriae.

11. A method for the prevention of urinary tract infections produced by fimbriated *E. coli* expressing type P fimbriae characteristic of CECT 4484 or expressing type 1 fimbriae characteristic of CECT 4485, comprising:

injecting a mammal with a member selected from the group consisting of Type P fimbriae isolated from *E. coli* CECT 4484, Type I fimbriae isolated from *E. coli* CECT 4485, and mixtures thereof;

thereby provoking an immune response by said mammal and increasing the titer of anti-fimbriae antibodies in blood of said mammal.

12. A method for the production of anti-fimbriae-adhesion antibodies for the diagnosis and typification of uropathogenic *E. coli* expressing type P fimbriae characteristic of CECT 4484 or type 1 fimbriae characteristic of CECT 4485, comprising;

immunizing a mammal with a member selected from the group consisting of Type P fimbriae isolated from *E. coli* CECT 4484, Type I fimbriae isolated from *E. coli* CECT 4485, and mixtures thereof;

collecting serum from said mammal; and isolating anti-fimbriae adhesion antibodies from said serum.

* * * * *